United States Patent [19]

Allen et al.

[11] 4,019,962

[45] Apr. 26, 1977

[54] APPARATUS FOR AEROBIC FERMENTATION

[75] Inventors: Richard L. Allen, Munster; Benny M. Benjamin, Skokie; Terry A. Lappin, Naperville; John A. Ridgway, Jr., La Porte; Elmer J. Saunders, Downers Grove, all of Ill.

[73] Assignee: Standard Oil Company (Indiana), Chicago, Ill.

[22] Filed: Aug. 11, 1975

[21] Appl. No.: 603,460

[52] U.S. Cl. .............................. 195/142; 195/139; 195/143
[51] Int. Cl.$^2$ ......................................... C12B 1/00
[58] Field of Search .......... 195/127, 139, 142–144, 195/115, 109; 209/211

[56] References Cited

UNITED STATES PATENTS

| 3,625,834 | 12/1971 | Muller .................. 195/142 |
| 3,705,082 | 12/1972 | Hondermarck et al. .......... 195/107 |
| 3,847,750 | 11/1974 | Ridgway, Jr. et al. ............. 195/142 |
| 3,869,559 | 3/1975 | Clark .................. 209/211 |

Primary Examiner—R. B. Penland
Attorney, Agent, or Firm—Gregory E. Croft; Arthur G. Gilkes; William T. McClain

[57] ABSTRACT

Improved apparatus for the continuous aseptic growth of single-cell protein materials, employing an aqueous ethanolic substrate fortified with nutrient elements, preferably under oxygen limited conditions. The fermentation is conducted under conditions which afford effective means of attaining high rates of oxygen transfer and heat removal coupled with intense agitation.

13 Claims, 3 Drawing Figures

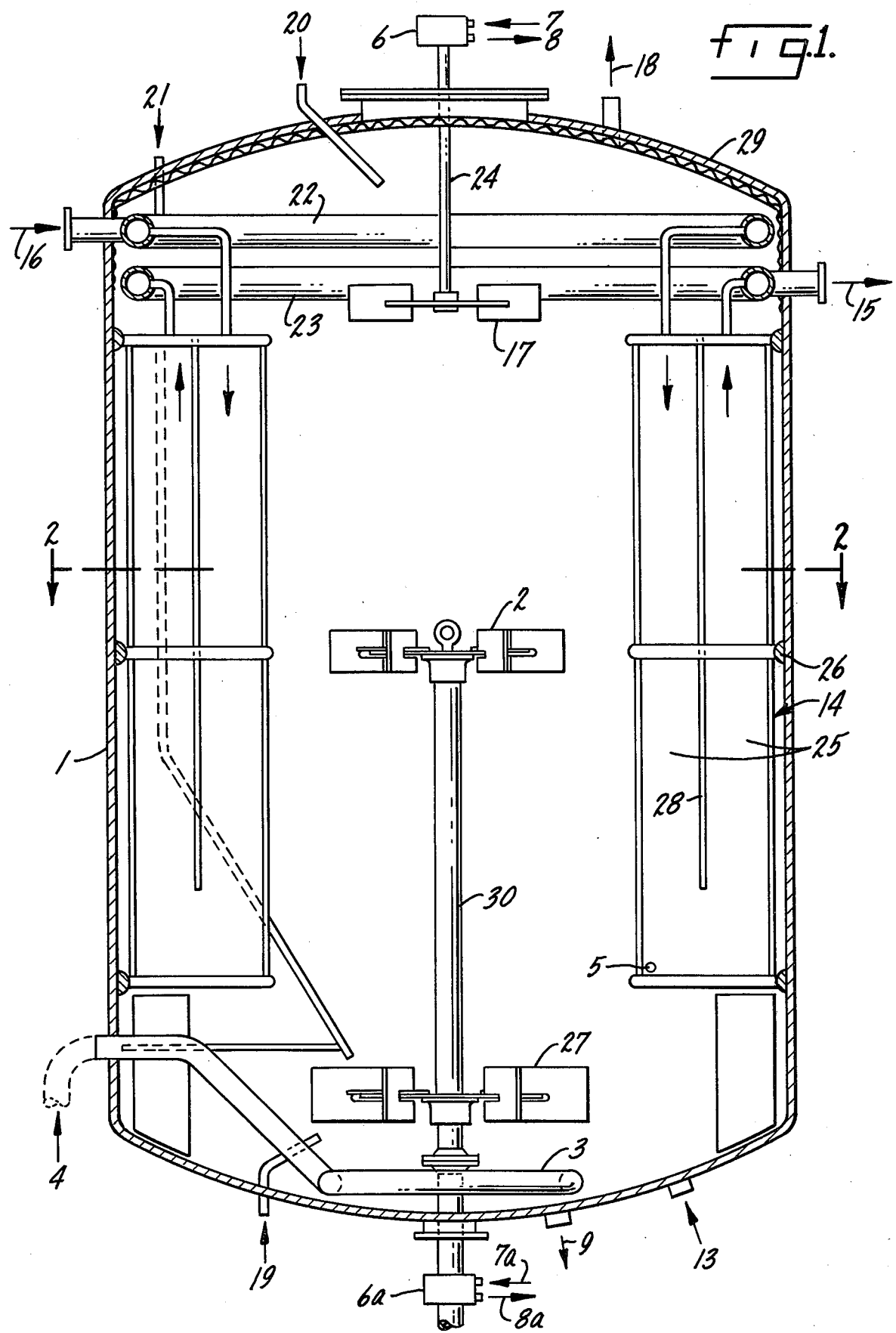

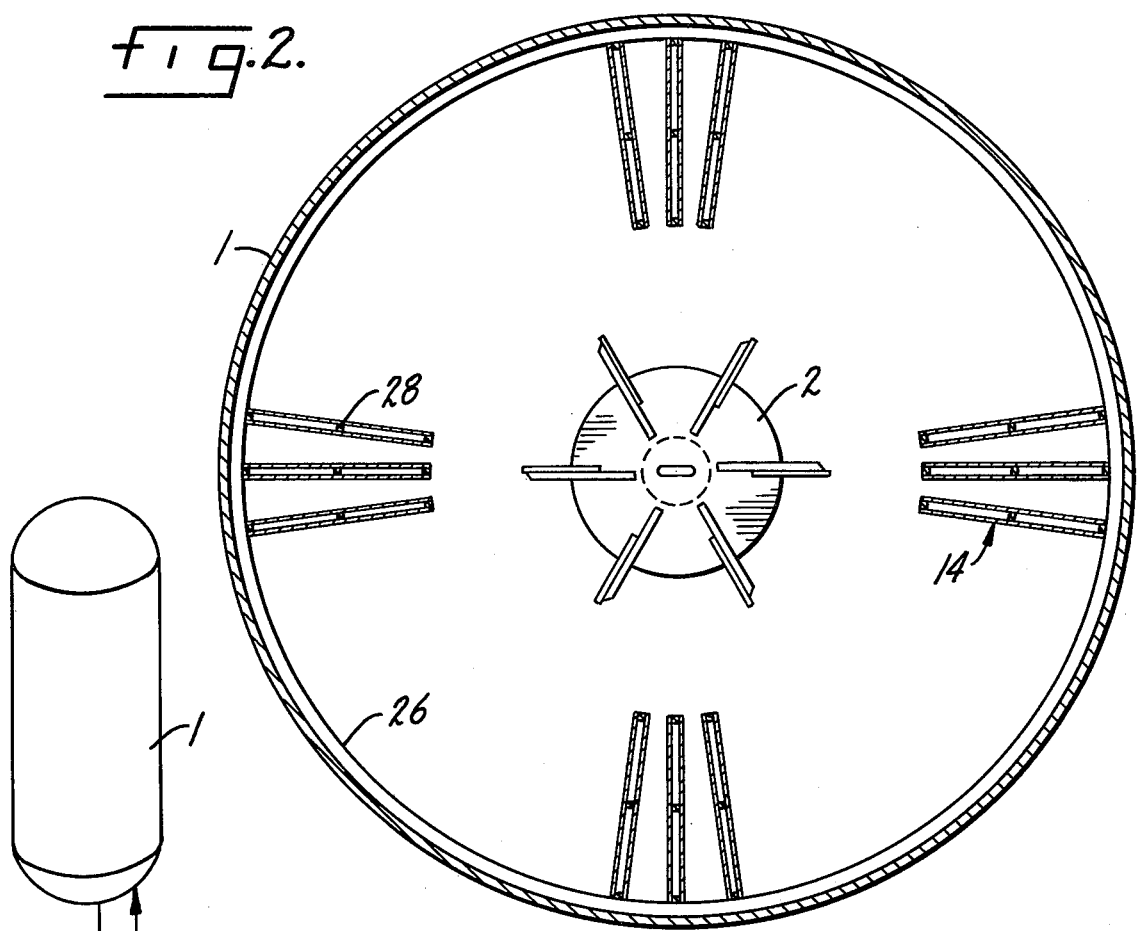
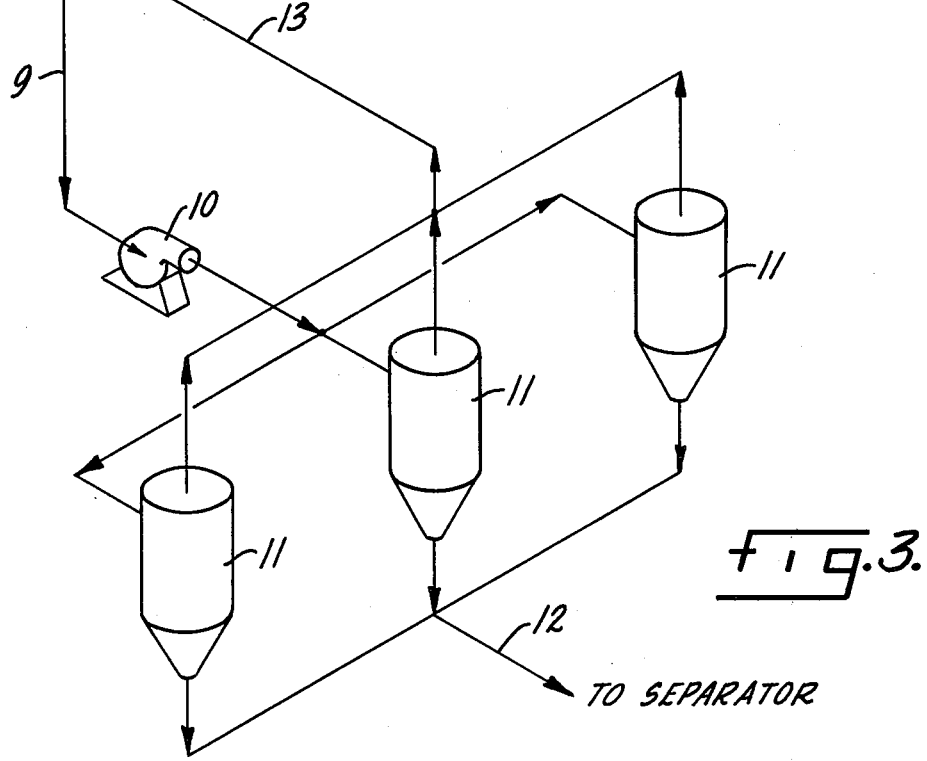

4,019,962

APPARATUS FOR AEROBIC FERMENTATION

BACKGROUND OF THE INVENTION

Recent concern for the welfare of the world population has included consideration of additional means for feeding the rapidly increasing number of people involved. The problem embraces providing both adequate per capita caloric intake and a balanced diet, with particular reference to the acknowledged lack of sufficient protein-affording foods in many parts of the world. One means for providing necessary protein supplies is through the growth of single-cell protein affording microorganisms, such as yeast, bacteria and algae, for use as either foods or food supplements.

Production of single-cell protein (SCP) materials in large quantity may be accomplished by fermentation processes employing, for example, carbohydrate, hydrocarbon or oxygenated hydrocarbon materials as substrate. Principal requirements are that the substrate material be inexpensive and readily consumed by the selected microorganism so that process costs are not excessive. Equally important is the acceptability and utility of the SCP material, including yeasts, as a food or food component. The latter considerations include taste and odor factors relating to public acceptance as well as metabolic and toxicity factors relating to suitability of SCP material for inclusion in the human diet.

Both the technical and the patent literature describe fermentation processes for production of microorganisms which readily afford useful SCP materials. For example, yeasts have been grown on the polysaccharides contained in waste sulfite liquor and on the normal alkane components of a gas oil hydrocarbon fuel. Production of bacteria has been similarly described as, for example, in U.S. Pat. No. 3,546,071, which employs a mixture of oxygenated hydrocarbons, including ethanol, as substrate. Fermentation to produce yeasts or bacteria comprises an oxidation process, evolving much heat and requiring both substantial oxygen transfer and good control of fermentation temperature. Perferred substrate materials will already contain as much combined oxygen as possible in order to minimize the heat release and the oxygen requirement. Production of food-grade SCP material may also require an extraction step to limit the presence of undesirable, residual substrate material such as high-molecular-weight hydrocarbons or slowly fermented oxygenated hydrocarbon species.

Most of the fermentation processes planned or in use currently for production of SCP material are intended to provide primarily an animal feed supplement and hence to supply protein for human consumption only indirectly. However, certain microorganisms, notably yeasts within the Saccharomycetoideae and Cryptococcoideae sub-families, have been certified by the Food and Drug Administration for direct use in foods intended for human consumption.

One highly desirable substrate material is ethanol. It exhibits complete water solubility, is already in a partially-oxidized state, is itself acceptable for use in foods, and creates no problem as to removal from the produced microorganism cells. However, ethanol is a growth inhibitor to many microorganisms and some others do not grow well in its presence.

Other alcohols are also suitable substrates with certain yeasts. For example, French Pat. No. 2,006,235 describes the preparation of amino acids by the growth of various yeast strains on methanol.

The economics of SCP production require that the substrate material be relatively inexpensive. In comparison with waste materials employed as substrates in many commercial fermentations, ethanol is sufficiently expensive to require that it be used most efficiently if selected to serve as a substrate.

SUMMARY OF THE INVENTION

It is the purpose of this invention to provide an improved aerobic fermentation apparatus for the continuous production of food yeasts.

Another object of this invention is to employ optimally the inorganic nutrient materials necessary to the growth of the desired yeasts.

It is a further object of this invention to provide an economic source of high-quality protein material, for use as a food or food ingredient intended for human consumption, by utilizing the growth of a yeast having FDA approval for use in foods on a substrate possessing a high proportion of combined oxygen and being itself of acceptable food quality Specifically, a food yeast such as Candida utilis (Torula yeast) is grown on an ethanol substrate under conditions selected for maximum conversion of the substrate to a useful protein product.

Candida utilis (Torula yeast) is preferred because it gives a higher yield than other food yeasts and does not require growth factors, such as vitamins, as required by some others.

DESCRIPTION OF THE DRAWINGS

The attached drawings are illustrative of typical embodiments of this invention.

FIGS. 1, 2, and 3 describe an embodiment of apparatus particularly applicable to the practice of this invention.

FIG. 1 presents an elevational view partly in cross-section setting forth details of an eminently suitable internal cooling apparatus for use in the fermentation process of this invention.

The embodiment of the "hollow baffle" cooling apparatus shown in FIG. 1 is contained within fermentor vessel 1 which is conventionally fitted with macronutrient inlet 20, substrate inlet 21, micro-nutrient inlet 19, spent air outlet 18, foam knocker 17, coolant inlet 16, coolant outlet 15, flat blade turbine agitators 2 and 27, air sparger 3 with air inlet 4 attached thereto, double mechanical seals 6 and 6a having a bactericidal liquid, inlets 7 and 7a and outlets 8 and 8a, respectively, being connected to a circulating system, and broth line 9. The cooling apparatus comprises horizontal circular header pipes 22 and 23 having substantially the same mean diameter, interconnected through a plurality of vertical connecting hollow baffles illustrated by 14, arranged in parallel rows around the circumference of the header pipes 22 and 23. The connecting hollow baffles illustrated by 14 have a width of roughly 16% of the fermentor diameter and extend roughly two-thirds of the length of the fermentor vessel 1. The inlet coolant header 22 is attached to coolant inlet line 16 and outlet header 23 is attached to coolant outlet line 15, both of lines 15 and 16 extending through the wall of fermentor vessel 1.

In practice, water coolant enters the inlet header 22 through line 16 and is distributed to connecting hollow baffles illustrated by 14 which provide surface for heat transfer with the agitated fermentation broth contained in the fermentor vessel 1. The water increases in temperature as it absorbs heat from the broth, passing as heated water into the outlet header 23 through coolant outlet line 15. Head jacket 29 provides a means for refrigerating the top of the fermentor.

FIG. 2 provides a cross-section view of the cooling apparatus of FIG. 1, taken at horizontal plane A—A, showing the hollow baffles 14 positioned within the fermentor vessel 1 and each receiving a connection from both the outlet coolant header 23 and the inlet coolant header 22. The flat blade turbine agitator 2 is shown centrally situated within the fermentor vessel 1.

FIG. 3 illustrates the manner in which a plurality of hydroclones can be connected in a parallel arrangement. This figure represents the arrangement of the nonvaporlocking pump 10, hydroclone(s) 11, deaerated broth line 12 and froth line 13.

DESCRIPTION OF THE INVENTION

This invention embraces the aseptic growth of selected yeasts on an ethanol substrate in a specific and continuous manner, providing for optimized utilization of selected nutrient elements, including iron. The choice of ethanol as the sole source of carbon in the substrate substantially eliminates problems relating to production of protein material suitable for direct human consumption. Ethanol is readily available and accepted as a foodstuff. Its fermentation products will not contain toxic residual substrate. Its volatility assures that residual ethanol will be removed readily during drying of the microorganism product. Its solubility in water obviates multi-phase physical problems present with polysaccharide or hydrocarbon substrate materials.

More precisely, this invention relates to apparatus for continuous aerobic fermentation processes for growth of single-cell microorganisms, as shown in FIGS. 1, 2 and 3, comprising in combination: (a) a vertically-disposed, cylindrical fermentor vessel shell component (1) having an upper and lower section; (b) a coolant inlet means 16 attached to the inlet coolant header 22 and a coolant outlet means 15 attached to a the outlet coolant header 23, both said coolant means 15, 16 being situated near the upper end of the fermentor shell section to describe a continuous flow therethrough; c an inlet coolant header 22 and an outlet coolant header 23 positioned horizontally in the top section of the fermentor, each said header having a separate sealable attachment to a single chamber section 25 within the vertically aligned baffles 14; (d) a plurality of hollow baffles 14 having a partially partitioned interior section 28 extending from an upper position inside the baffle to a position near the bottom therein to create chamber sections 25 which permit the downward flow of coolant in one chamber section of the baffle and the upward flow of coolant in the remaining chamber section of the baffle, said baffles being supported by rings 26 which are attached to the inner-perimeter of the shell section and each baffle being equipped with a drain plug 5 near the bottom section; (e) entry means for substrate 21, macro-nutrient 20, and micro-nutrient 19; (f) a spent air outlet means 18 located in the upper head section; (g) a foam knocker 17 positioned within the upper head section and positioned 6 to 12 inches above liquid level, said knocker having a shaft 24 and positioned in relation to the macro-nutrient inlet such that a spray of macro-nutrient is developed that tranverses the fermentor cross section extending vertically through the upper head section; (h) two flat blade turbine agitators 2 and 27 having an agitator shaft 30 extending vertically into the fermentor vessel through the lower head section; (i) an air sparger 3 located in the lower section beneath the lowest flat blade turbine 27 being attached to an air inlet 4 entering from the lower shell section of the fermentor vessel; (j) double mechanical seals 6 and 6a located on the foam knocker and agitator shafts 24 and 30 outside the fermentor vessel, said seals having an entry means 7 and 7a for bactericidal liquid and exit means 8 and 8a, said entry and exit means being attached to means (not shown) for recirculating the liquid through a cooler; and (k) a non-vaporlocking circulating pump 10 attached to the lower exterior section of the fermentor vessel through the broth line 9 and connected to hydroclone unit (s) 11 having a froth line 13 attached to the fermentor vessel and a deaerated broth line 12 affording a discharge means for the deareated liquid broth.

The vertical length of the fermentor vessel contemplated within the scope of this invention ranges from 5 to 100 feet. Typically, the fermentation vessel has a vertical length of 15 to 50 feet, a diameter of about 10 to 45 feet, contains 40 to 100 hollow baffles and is interconnected with from 1 to 18 hydroclone(s), say 1 to 6, through a nonvaporlocking pump. When more than one hydroclone is used, they are connected in parallel.

The mixing compartment of the fermentor vessel is surrounded by a contiguous group of hollow baffles having a vertical length of about 4 to 80 feet, for example, 10 to 20 feet and a width of 1 to 10 feet, for example, 1 to 5 feet.

The flat-blade turbine agitator can be equipped with a plurality of flat blade turbines depending on the size of the fermentor vessel. Usually, one, two or three flat blade turbines are sufficient for fermentor vessels having a vertical length of about 15 to 50 feet and a diameter of 10 to 45 feet.

Many yeasts do not grow on alcoholic substrates and growth on one alcohol, e.g. methanol, does not permit the generalization that the same yeast will grow well on a second alcohol, e.g., ethanol. Suitable yeasts which do metabolize ethanol include those listed in Table I.

TABLE I

SUITABLE YEASTS FOR USE WITH ETHANOL SUBSTRATE

*Saccharomyces cerevisiae*
*Saccharomyces lactis*
*Saccharomyces fragilis*
*Hansenula miso*
*Pichia farinosa*
*Candida utilis*

Preferred yeasts include Saccharomyces cerevisiae, Saccharomyces fragilis, and Candida utilis. These are preferred because they already possess FDA approval for use in foods intended for human consumption. Indeed, Candida utilis has been recognized as an edible protein source for many years.

Aerobic growth of the selected yeast is effected on a large scale in a continuous, aseptic fermentation process wherein sterile substrate, nutrients and oxygen are introduced continuously into a fermentor vessel while fermentation broth is continuously removed. Growth is maintained by control of the dilution rate (space velocity) through controlled addition of water to the fermentor. Suitable control devices are employed to maintain substantially steady-state conditions. Where the scale of yeast production is sufficiently large, it may be desirable to employ a plurality of fermentors in parallel arrangement. Fermentor effluents may thereafter be combined for subsequent downstream processing.

Within the fermentation zone ethanol is maintained as an aqueous substrate having a concentration in the range from 50 to 3000 ppm, preferably from 100 to 500 ppm and most preferably about 200 ppm. Inorganic nutrients are maintained in the fermentation broth by continuous addition of aqueous solutions of suitable compounds containing the nutrient elements to provide the ratios shown in Table II. Those nutrients supplied in relatively large amounts are classified as macro-nutrients. In contrast, those nutrients required or assimilated in small or "trace" amounts are classified as micro-nutrients.

TABLE II
INORGANIC NUTRIENTS IN FERMENTATION BROTH

| Nutrient Element | Typical Compound | Nutrient Element Input | |
|---|---|---|---|
| | | Broad Range | Preferred Range |
| Macro-nutrients | | — gm/100 gm cells produced — | |
| Phosphorous | $H_3PO_4$ | 1–5 | 1.5–3 |
| Potassium | KOH | 1–5 | 1.5–3 |
| Magnesium | $MgSO_4$ | 0.1–1 | 0.2–0.5 |
| Calcium | $CaCl_2$ | 0.001–1 | 0.01–0.05 |
| Micro-nutrients | | — ppm of cells produced — | |
| Iron | $Fe_3[C_3H_4(OH)(COO)_3]_2$ | 30–1000 | 50–300 |
| Zinc | $ZnSO_4$ | 10–500 | 20–150 |
| Manganese | $MnSO_4$ | .5–30 | 1–10 |
| Molybdenum | $Na_2MoO_4$ | 10–500 | 20–150 |
| Iodine | KI | 1–100 | 10–50 |
| Copper | $CuSO_4$ | .5–15 | 1–5 |

During the fermentation process ethanol is consumed with evolution of carbon dioxide gas and an increase in the acidity of the fermentation medium. Nitrogen is essential to the growth of the microorganisms and is conventiently added to the fermentation broth as either anhydrous or aqueous ammonia. Being an alkaline reagent, the addition of nitrogen as ammonia also serves to decrease acidity in the fermentation broth. The pH of the medium is maintained in the range from 2.5 to 6.5, preferably from 3.5 to 5.5 and most preferably at about 4.0. This pH control is achieved by controlled addition of ammonia.

The added inorganic nutrients are effective in promoting yeast growth only to the extent of their solubility in the fermentation broth. The requirement for phosphorus is customarily satisfied by addition of a phosphate salt of phosphoric acid. When iron is also required in the aqueous mixture of nutrients, iron phosphate precipitates making iron less available to the fermentation process. It has now been found that an improved rate of yeast growth can be achieved by separately adding the micro-nutrient elements, including iron, to the broth. Iron is preferably introduced as the water-soluble salt of an organic polycarboxylic acid and most preferably as iron citrate. This salt may be formed in the aqueous solution by the appropriate additions of an inorganic iron salt, such as ferric chloride, ferrous sulfate, ferric sulfate and ferric nitrate, and citric acid.

All liquid streams are sterilized by heating to about 300° F. under about 70 psig pressure or by passing them through sterilizing filters prior to addition to the fermentor. Sterilization may also be accomplished by direct steam injection. No separate sterilization is normally required for the ammonia steam. When added as a gas, ammonia may conveniently be injected into the entering compressed air stream at a point upstream of the sterilizing filter.

Air, optionally enriched with oxygen, is compressed and sterilized by filtration through a series of small-pore or membrane-type filters. When mixed with ammonia the mixed gases are passed through the filter zone.

It is contemplated within the scope of this invention that a suitable sterile antifoaming agent can be injected into the nutrient stream if needed.

Care should be taken to maintain all sterile input streams at a higher pressure than non-sterile streams during heat exchange. Similarly the fermentor should be operated at a positive, superatmospheric pressure to prevent contamination with non-sterile materials and cooling water to the baffles should be controlled at a pressure below that of the fermentor.

Prior to initiating the fermentation all equipment should be sterilized. For example, it is preferred that the fermentor and all lines intended to pass sterile streams be treated for about 20 minutes with steam at a temperature of about 250° F. To sterilize the seal area, the cavity between the mechanical seals is normally filled with bactericidal solution or pressurized with steam. Additionally, steam is injected into the steam jacket around the mechanical seal to assure achievement of the sterilization temperatures. To make sure that the massive agitator shaft and mechanical seal attain the sterilization conditions, a hollow shaft can be used through which steam is permitted to circulate.

In starting a fermentation, an initial loading of the fermentor with aqueous substrate, ammonia and nutrient elements is followed by innoculation of this aqueous medium with a culture of the selected yeast. Air is then sparged into the fermentor, usually with additional mechanical agitation provided. The fermentation zone is maintained at a temperature in the range from 80° to 110° F., and preferably about 90° to 100° F., while the top pressure is maintained within the range from 2 to 20 psig, preferably about 10 psig, to assist in preserving aseptic conditions. The initial slow growth of the yeast is superseded after a few hours by the rapid exponential growth which is thereafter maintained in the fermentor by withdrawal of fermentation broth, comprising aqueous medium and suspended cell product, at a rate selected to maintain a cell concentration in the range from 1.5 to 5.0 wt.%, generally above about 2.0 wt.% and preferably about 3.0 wt.%, suspended in the fermentation liquor. The withdrawal rate maintaining this cell concentration should provide an average residence time for fermentation liquor in the fermentation zone in the range from 2 to 4 hours and preferably about 3 hours. Stated in different terms, the dilution rate should be in the range from 0.25 to 0.50/hr. and preferably should be about 0.33/hr.

Liquid level in the fermentor is maintained by withdrawing fermentation broth. The aqueous nutrient solution is charged at a rate to maintain the desired dilution rate, while ethanol and ammonia are added at rates to preserve the desired concentration levels and acidity. The withdrawn fermentor broth is sent to ade-aeration stage to remove entrained gases from the fermentor effluent and send nearly clear broth to the separation stage. The de-aeration stage consists of several hydroclones in parallel. Circulation of the broth through the hydroclones subjects the liquid to high centrifugal forces resulting in separation of liquid from the lighter broth which is returned to the fermentor. The use of multiple hydroclone units in parallel ensures high centrifugal forces for more effective separation. Advantages of this apparatus include no moving parts and no available entry point as a source of contamination. The clear broth is sent to a separation stage, preferably a centrifuge, for recovery of the cell product. The aqueous fermentation liquor discharged from the centrifuge may contain sufficient ethanol together with nutrient elements and ammonia to make this stream suitable for recycle. In a typical recycle operation about 80% by volume of this stream is admixed with the continuously added streams after a suitable sterilization. The 20 vol.% discard serves to prevent buildup of less desirable inorganic ions such as chloride in the fermentation liquor.

The yeast cell product recovered from the separation zone may be washed with water, pressed and dried as required by the end use intended for the protein material.

An excess of sterile compressed air is supplied to the fermentor after passage through a filtration zone. Oxygen utilization is usually in the range from 25 to 60% of input and most frequently about 33%.

The concentration of dissolved oxygen in the fermentation liquid should be within the range from 0.1 to 0.3 ppm under oxygen-limiting conditions and may range as high as 1 to 4 ppm when operating under ethanol-limiting conditions. Some foaming occurs in the fermentor but at the preferred low ethanol concentrations the foaming is not severe. However, the fermentor vessel is equipped with a foam-knocker which consists of a flat-blade turbine rotating at a speed sufficiently high to cause foam throw to the vessel wall thereby breaking the bubbles on the foam surface and thus preventing the foam from rising into the spent air outlet. The input nutrient stream can be directed onto the foam-knocker to further help in foam control. Therefore, the regular use of surface active agents for foam control which cause unacceptable oxygen transfer rate reduction and possibly unwanted product quality reduction is avoided. Effluent air, containing product carbon dioxide, is exhausted from the fermentation zone through a pressure-responsive regulating valve, to maintain fermentor pressure and prevent entry of non-sterile materials which would contaminate the fermentor contents.

When the effluent gas stream contains a significant concentration of ethanol vapor it is desirable to pass this effluent through a water scrubber to recover the ethanol, later employing the ethanolic water as makeup to the fermentor.

The heat of fermentation is approximately 10,000 B.t.u./lb. cells so that temperature control within the range from 80° to 100° F. requires extensive cooling. Where water is available at a sufficiently low temperature, cooling may be effected by once-through water circulation through cooling elements contained within the fermentation zone. In other circumstances a closed refrigeration system employing a refrigerant non-toxic to the system is preferred. Suitable refrigerants include ammonia and the freons. These refrigerants can be directly used in the hollow baffles and thereby eliminates the need for a separate evaporator and coolant brine in the refrigeration unit. Also, the higher heat transfer coefficients of boiling liquids (as compared with single phase coolant) enables lower baffle surface area requirements. A small amount of leakage into the fermento will present no adverse effects. The use of boiling ammonia is especially advantageous. Leakage into the vessel will result in lower direct ammonia usage in the air such that it acts as an automatic leak detector. It also has a much higher latent heat of evaporation compared with Freon or other refrigerants; thus a smaller amount needs to be circulated.

A particularly effective cooling element for use in any vertical cylindrical fermentor vessel and particularly with the process of this invention comprises two circular circumferential header tubes fitted horizontally within the fermentor and connected by a plurality of vertical hollow baffles. The vertical baffles are arranged in rows about the circumference of the header tubes. Coolant circulates through the baffles which provide a large surface area for effective heat transfer. The hollow baffles are installed for the removal of heat. The intense agitation causes broth flow across the baffles allowing high heat transfer coefficients. Alternative cooling medium flow patterns for the internal baffles are available. Headers for the introduction of cold coolant are designed to minimize pressure difference between the baffles. The design assists a maintaining a lower pressure in the baffles than the corresponding point in the fermentor vessel so that when cold water or brine is used as a coolant, the possibility of leakage into and contamination of the fermentor is reduced. Boiling ammonia is preferred for it has a high latent heat of vaporization, relatively low boiling point at fermentor pressure. When using ammonia, leakage into the fermentor is detectable and causes no contamination or upset at low leakage levels.

Contamination of the fermentor during continuous operation is avoided by: (1) sterilizing all fermentor input streams, (2) sterilizing the mechanical seal coolant fluid, (3) preventing backflow of effluent streams, and (4) using aseptic techniques for all sampling. As discussed previously, all input streams are sterilized by heat or filtration. The mechanical seals on the fermentor agitator shaft, foam knocker shaft, and discharge pump are double mechanical seals. The seal coolant is a bactericidal fluid which is also sterilized by either heat or filtration. Therefore any inboard seal leakage consists of sterile material that will not contaminate the fermentor. Backflow of effluent streams is prevented by use of check valves and proper piping design.

The head jacket serves as a means for refrigerating the top of the fermentor. In continuous operation, the gradual accumulation of cell debris on unwetted surfaces can become a problem. It can build up to the point that it will flake off in pieces varying in size from those that will plug screens down to particles passed by the screens and included in the product. These latter differ in physical appearance as well as size from the normal yeast so that they appear in the product as foreign particles. This accumulation of debris also increases the problem of maintaining ascepsis. A vigorously growing continuous culture is subject to contamination only by those organisms that can grow at a sufficient rate to avoid washout. Slow growing aerobes and anaerobes can thrive in the debris, where they need not overcome continuous dilution by fresh nutrient solution. The presence of these foreign organisms does not interfere with the main fermentation but the particles, sluffed off into the broth and harvested with the product, carry with them large populations of foreign organisms that contaminate that product. This is especially true when the foreign organisms are spore formers; spores are not killed in subsequent pasteurization and drying operations.

Some fermentor designs use a spray of nutrient to flush the top surfaces of the fermentor. We have abandoned this approach; it is nearly impossible to wash all parts with a spray system and problems with carryover of spray droplets into the effluent spent air stream develop. The present design utilizes a simple and extremely effective mechanism. Cooling jackets and coils have been installed on all parts of the fermentor above the fluid level so that they can be cooled below the dew point of the spent air. Under these conditions all exposed surfaces are gently bathed by the continuous condensation of moisture. Surprisingly this is extremely effective in preventing adherence of cell debris and results in a cleaner fermentor than could be achieved by a spray washing system.

Food industry practice should be followed in selecting equipment for use in the fermentation process of this invention. A minimum of Type 304 stainless steel should be employed on all equipment which comes in contact with a sterile ingredient or which must be cleaned for sanitation.

The yield of yeast cells, based on ethanol substrate consumed, is generally within the range from 65 to 90 wt.%, the higher yields being achieved under oxygen-limiting rather than ethanol-limiting conditions. For either type of operation maximum cell yield is obtained at a dilution rate in the range from 0.25 to 0.4/hr.

The yeast cells produced typically contain about 40 to 60 wt.% protein, together with polysaccharides, especially in the cell wall, and some nucleic acids. A representative analysis includes:

| | |
|---|---|
| Nitrogen, total | 9.2 wt. % |
| Nitrogen, protein | 7.8 wt. % |
| Carbon | 45.4 wt. % |
| Hydrogen | 6.7 wt. % |
| Phosphorus | 2.0 wt. % |
| Ash | 8.9 wt. % |

A typical amino acid profile and a typical vitamin content of Torula food yeast grown on ethanol are presented respectively in Tables III and IV.

Accordingly, a highly nutritive food or food ingredient comprising SCP material is made available by the practice of this invention.

EXAMPLES

The following examples illustrate, without any implied limitation, the practice of this invention.

TABLE III

AMINO ACID PROFILE OF
ETHANOL GROWN TORULA YEAST

| | % of cell weight |
|---|---|
| Lysine | 3.5 |
| Histidine | 1.0 |
| Arginine | 3.5 |
| Aspartic Acid | 3.9 |
| Threonine | 2.3 |
| Serine | 2.1 |
| Glutamic Acid | 7.9 |
| Proline | 2.0 |
| Glycine | 2.5 |
| Alanine | 2.9 |
| Cystine | 0.3 |
| Valine | 2.6 |

TABLE III-continued

AMINO ACID PROFILE OF
ETHANOL GROWN TORULA YEAST

| | % of cell weight |
|---|---|
| Methionine | 0.5 |
| Isoleucine | 2.1 |
| Leucine | 3.4 |
| Tyrosine | 1.6 |
| Phenylalanine | 1.8 |
| Tryptophane | 0.02 |
| (Ammonia) | 1.4 |

TABLE IV

TYPICAL VITAMIN CONTENT OF ETHANOL GROWN TORULA YEAST

| | | |
|---|---|---|
| Biotin | 1.3 | microgram/gm. |
| Folic Acid | 10.6 | " |
| Inositol | 4.7 | " |
| Niacin | 387 | " |
| Pantothenic Acid | 211 | " |
| Panthenol | 200 | " |
| P-Aminobenzoic Acid | 3.0 | " |
| Riboflavin | 49 | " |
| Vitamin B-6 | 42 | " |
| Vitamin B-12 ca | 0.010 | " |
| Cholin Chloride | 5.1 | mg./gm. |
| Vitamin A | 500 | microgram/lb. |

EXAMPLE I

In a 4-liter glass fermentor was placed 3 liters of aqueous mineral nutrient solution medium containing:

| | |
|---|---|
| $KH_2PO_4$ | 1.0 g./liter |
| $K_2HPO_3$ | 1.0 g./liter |
| $NH_4Cl$ | 1.0 g./liter |
| $MgSO_4$ | 1.0 g./liter |
| $CaCl_2$ | 0.15 g./liter |
| $CuSO_4 \cdot 5H_2O$ | 0.0001 g./liter |
| $KI$ | 0.0002 g./liter |
| $MnSO_4 \cdot H_2O$ | 0.0009 g./liter |
| $Na_2MoO_4 \cdot 2H_2O$ | 0.0004 g./liter |
| $ZnSO_4 \cdot 7H_2O$ | 0.0014 g./liter |

To this medium was added 30 ml. ethanol and $FeCl_3$ (0.001 g./liter). Sterilized filtered air was sparged in with agitation to obtain an oxygen absorption rate in the range from 100 to 140 millimoles/liter/hour. The fermentor temperature was maintained at 30° C. and the pH was adjusted to 4.6 by addition of ammonia.

Freshly grown Torula yeast (Candida utilis) (50 ml. of 1% suspension) from a shaker culture was added to the fermentor. Cell growth was followed by measurement of optical density during the aseptic batch fermentation. Active cell growth started after about 3 hours and stopped when the cell concentration reached 0.7 g./100 ml. suspension.

The product was harvested by centrifugation and dried at 100° C. in an oven. The dry product was light brown in color and had a nutty flavor.

EXAMPLE II

The procedure of Example I was followed. When the cell concentration reached 0.6 g./100 ml, mineral nutrient solution, ammonia and ethanol were pumped into the fermentor at a steady rate while withdrawing fermentation broth to maintain a space velocity of 0.3/hr. Cell concentration in the effluent was maintained at 0.6 – 0.7 g./100 ml.

EXAMPLE III

Continuous growth of Candida utilis, A.T.C.C. No. 9256, was effected in a 28-liter fermentor vessel. After initial sterilization with steam the fermentor was loaded with an aqueous nutrient medium containing:

$H_3PO_4$ (85%) 3.24 g./liter;
KOH 1.28 g./liter;
NaOH 0.02 g./liter;
$MgSO_4$ 1.30 g./liter;
$CaCl_2.2H_2O$ 0.48 g./liter;
$FeCl_3.6H_2O$ 1.55 mg./liter;
$CuSO_4.5H_2O$ 0.10 mg./liter;
KI 0.21 mg./liter
$MnSO_4.H_2O$ 1.84 mg./liter;
$Na_2MoO_4.H_2O$ 0.41 mg./liter;
$ZnSO_4.7H_2O$ 1.00 mg.liter;

Ethanol was added to provide a concentration of 0.2 wt.% (2000 ppm). Initially aqueous ammonia was added as a 30% solution in the amount of 1 ml./liter and was added thereafter as required to maintain pH of 4.0 in the fermentor. An inoculum growth in a batch fermentor was added to provide a cell concentration of 0.1 g./100 ml. and allowed to grow at 90° F. through several doubling cycles as in a batch run. Addition of nutrient solution and ethanol and continuous withdrawal of fermentor broth through a bottom draw-off line was then begun and maintained at a dilution rate of 0.33/hr. Throughout the run air was sparged in and the concentration of dissolved oxygen was maintained at approximately 10 ppm.

In continuous operation a cell concentration of only 0.6 g./100 ml. broth (essentially 0.6%) was achieved.

EXAMPLE IV

The continuous run of Example III was repeated except for a separate addition of the nutrient element iron apart from other components of the aqueous nutrient medium. The iron (Fe+++) was stabilized in aqueous solution as a complex with citric acid.

In continuous operation, employing this modified nutrient addition system, the cell concentration lined out at 2.1 g./100 ml. broth (ca 2.1 wt.%). The cell yield, based on ethanol consumed, was 80.1 wt.%. The doubling time was 2.2 hours. Harvested dry cells were produced at a rate of 0.34 lb./hr./cu. ft. fermentor volume.

EXAMPLE V

The procedure of Example IV was generally followed except for varying the concentration of dissolved oxygen and ethanol to provide periods of oxygen-limited and ethanol-limited operation at selected-dilution rates ranging from 0.25 to 0.47/hr.

The oxygen concentration in the broth was about 0.3 ppm under oxygen-limited conditions which gave significantly better utilization of ethanol. In ethanol-limited operation the ethanol concentration was only about 40 ppm.

TABLE V

CELL GROWTH ON ETHANOL

| | Dilution Rate, hr.$^{-1}$ | | | | |
|---|---|---|---|---|---|
| | 0.25 | 0.33 | 0.4 | 0.44 | 0.47 |
| $O_2$-Limited | | | | | |
| Cell yield[a] | 83.8 | 84.0 | 82.8 | 71.5 | — |
| N. wt. % | 8.7 | 8.9 | 9.1 | 9.2 | — |
| Protein, wt. %[b] | 45.0 | 44.6 | 47.3 | 46.7 | — |
| EtOH-Limited | | | | | |
| Cell yield[a] | 71.6 | 72.1 | 70.3 | 65.6 | 62.5 |
| N. wt. % | 8.9 | 9.3 | 9.1 | 9.1 | 9.6 |
| Protein wt. %[b] | 46.8 | 46.2 | 45.7 | 44.4 | 47.2 |

[a]Wt. % on ethanol consumed.
[b]Calculated value (N−0.153 × Nucleic Acid) × 6.25

EXAMPLE VI

In the continuous production of Torula yeast (Candida utilis), grown on a substrate containing ethanol as the sole source of carbon, at the rate of 1,971 lbs./hr., there are provided two aerobic fermentors, each having a capacity of 25,000 gallons, arranged in two production trains. Each fermentor vessel has a diameter of 14 feet and a straight side height of 20 feet. The use of several fermentors provide flexibility so that contamination of one fermentor still permits the plant to keep functioning.

In the process, ethanol (92.5 vol. %: 400 gal./hr.) is sterilized by filtration and sent to the fermentors. A solution of macro-nutrient salts (1453 gal./hr.) is combined with make-up water (5316 gal./hr.). The mixture is continuously sterilized by heating with steam to 275° F. The macro-nutrients are first dissolved in water to provide an aqueous concentrate which is ten pumped to the mixing tank to provide the following feed rates for the component nutrients.

| MACRO-NUTRIENTS | | lb./hr. |
|---|---|---|
| Phosphoric Acid | 75% solution of $H_3PO_4$ | 181 |
| Potassium Hydroxide | 45% solution of KOH | 156 |
| Magnesium Sulfate | $MgSO_4 . 7H_2O$ | 141 |

The micro-nutrients are similarly provided as an aqueous concentrate, sterilized and pumped directly to the fermentor to provide the following feed rates for the component nutrients.

| MICRO-NUTRIENTS | | lb./hr. |
|---|---|---|
| Citric Acid | $C_3H_4(OH)(COOH)_3$ | 3.43 |
| Ferric Sulfate | $Fe_2(SO_4)_3 . 9H_2O$ | 1.23 |
| Manganous Sulfate | $MnSO_4 . 4H_2O$ | 0.05 |
| Zinc Sulfate | $ZnSO_4 . 7H_2O$ | 0.65 |
| Sodium Molybdate | $Na_2MoO_4 . 2H_2O$ | 0.31 |
| Potassium Iodide | KI | 0.06 |
| Cupric Sulphate | $CuSO_4 . 5H_2O$ | 0.02 |

Cooled sterile liquid is sent to the continuous fermentors operated at 90° F. under aseptic conditions. Air required for the fermentation is sterilized by passage through membrane-tupe filters and sparged into the bottom section of each fermentor where oxygen transfer is effected by intense agitation of the fermentation broth. Sterile air is introduced to each fermentor at a rate of 3,400 standard cubic feet/minute and oxygen transfer is effected with a turbine agitator. Anhydrous ammonia is added continuously to the fermentors as a nutrient with the air, supplying the nitrogen content of the cells, in the total amount of 202 lbs./hr. which is sufficient to maintain the acidity level at pH 4.0.

Each fermentor is put on stream with addition of a starter culture of viable Candida utilis yeast cells grown in a batch seed tank.

Each fermentor is operated in the exponential phase of growth at 90° F. and pH 4.0, effecting a doubling of cell weight every 2.1 hours. Residence time in the fermentors is 3 hours.

Spent air containing unabsorbed oxygen and product carbon dioxide is released through a regulating valve. The heat of fermentation is removed by passage of cold water through a hollow baffle cooling element of the type shown schematically in FIGS. 1 and 2.

Total fermentor effluent, amounting to 60,000 lb./hr. of fermentation broth containing 3.3 wt.% yeast cells, is separated by centrifuging into a yeast cell cream (11,000 lb./hr. containing 18.0 wt.% yeast cells) and a supernatant aqueous solution containing residual ethanol and nutrient elements. The supernatant solution (49,000 lb./hr.) is sent to discard for waste processing.

The yeast cream is sent directly to a spray drier after pasteurization, recovered as a powder containing 5.0 wt.% moisture, and sent to storage.

We claim:

1. Apparatus for continuous aerobic fermentation processes for growth of single-cell microorganisms including a vertical cylindrical fermentor vessel shell component (1) having an upper and lower section, which has attached thereto:
    a. a coolant inlet means (16) extending inside through the wall of said vessel shell component and attached to the inlet coolant header (22) located within said shell component, and a coolant outlet means (15) extending inside through the wall of said vessel shell component and attached to the outlet coolant header (23) located within said shell component, both said coolant means (15, 16) being situated near the upper end of the fermentor shell section to describe a continuous flow therethrough;
    b. the said inlet coolant header (22) and said outlet coolant header (23) are positioned horizontally in the upper section of the fermentor, each said headers having a separate sealable attachment to a single chamber section (25) within the vertically aligned hollow baffles (14) located within said vessel shell component;
    c. the plurality of said hollow baffles (14) have a partially partitioned interior section created by the vertical shield (28) extending from an upper position inside the baffle to a position near the bottom therein to create chamber sections (25) which permit the downward flow of coolant in one chamber section of the baffle and the upward flow of coolant in the remaining chamber section of the baffle, said baffles being fitted with support mounts (26) to the inner-perimeter of the shell section in a vertical alignment and equipped with a drain plug (5) near the bottom section of the baffles;
    d. the entry means for substrate (21), and macro-nutrient (20), being attached to the upper head section extending inside said vessel shell component;
    e. the entry means for micro-nutrient (19) being attached to the lower shell section, extends inside said vessel shell component;
    f. the head jacket (29) being located along the inner perimeter of the upper head section said head jacket consisting of cooling jackets and coils;
    g. the spent air outlet means (18) attached to the upper head section, extends inside said vessel shell component;
    h. the foam knocker (17) positioned within the upper head section adjacent to said inlet and outlet coolant headers (22, 23), said knocker having a shaft (24) extending vertically through the top shell section;
    i. the flat blade turbine agitators (2) and (27) having an agitator shaft (30) extending vertically into the fermentor vessel through the lower shell section;
    j. the air sparger (3) located inside the lower shell section beneath the lowest most flat blade unit (27) which is attached to an air inlet (4) entering from the lower shell section of the fermentor vessel;
    k. the double mechanical seals (6) and (6a) are located on the said agitator and foam knocker shafts (24) and (30) outside the fermentor vessel, said seals (6) and (6a) having entry means (7) and (7a) and exit means (8) and (8a) for bactericidal liquid; and
    l. the non-vaporlocking circulating pump (10) is attached to the lower exterior section of the fermentor vessel through the broth line (9) extending from within the fermentor vessel and connected to hydroclone unit(s) (11) which has a froth line (13) attached to the exterior section of the fermentor vessel and a de-aerated broth line (12) affording a discharge means for the liquid broth from said pump.

2. The apparatus of claim 1 wherein the cooling jackets and coils are capable of being cooled below the dew point of the spent air passing through the upper section of the fermentor.

3. The apparatus of claim 1 wherein the vertical length of the fermentor vessel is within the range from about 5 to about 100 feet.

4. The apparatus of claim 1 wherein the fermentor vessel encloses at least two hollow baffles.

5. The apparatus of claim 1 wherein the flat blade turbine agitator has at least one flat blade unit and at least one air sparger located beneath the lowest situated flat blade unit.

6. The apparatus of claim 1 wherein 1 to 18 hydroclone units are connected in parallel to the non-vaporlocking circulating pump.

7. The apparatus of claim 1 wherein the vertical length of the fermentor vessel is about 15 to 25 feet and the diameter is about 10 to 20 feet, said vessel containing 40 to 60 hollow baffles, and having 1 to 5 hydroclone units connected in parallel to the non-vaporlocking circulating pump.

8. The apparatus of claim 1 wherein a contiguous group of hollow baffles is supported on the inner perimeter of the shell section and the air sparger is situated centrally within the lower end of the fermentor vessel.

9. The apparatus of claim 1 wherein the vertical length of the hollow baffles is within the range from 10 to 20 feet and the width is within the range of 1 to 5 feet.

10. The apparatus of claim 1 wherein the inlet coolant header and outlet coolant header are positioned below the foam knocker and above the tops of the hollow baffles.

11. The apparatus of claim 1 wherein the flat-blade turbine agitator has one, two or three flat blade units.

12. The apparatus of claim 11 wherein the flat-blade turbine agitator has two flat blade units.

13. Apparatus for continuous aerobic fermentation processes for growth of single-cell microorganisms comprising a fermentor vessel shell component having an upper and lower section, wherein the cooling element consists of two circular circumferential header tubes fitted horizontally within the fermentor and connected by a plurality of vertical hollow baffles having a partially partitioned interior section created by a vertical shield extending from an upper position inside the baffle to a position near the bottom therein to create chamber sections which permit the downward flow of coolant in one chamber section of the baffle and the upward flow of coolant in the remaining chamber section of the baffle, said baffles being arranged about the circumference of said head tubes and a head jacket, located along the inner perimeter of the upper head section, containing cooling jackets and coils.

* * * * *

UNITED STATES PATENT OFFICE
CERTIFICATE OF CORRECTION

Patent No. 4,019,962              Dated April 26, 1977

Inventor(s) Richard L. Allen, Benny M. Benjamin, Terry A. Lappin, John A. Ridgway, Jr., and Elmer J. Saunders It is certified that error appears in the above-identified patent and that said Letters Patent are hereby corrected as shown below:

| | | | |
|---|---|---|---|
| Column 2, | line 23 | After "quality" add -- . --. | |
| " 3, | " 43 | "to a the" should be -- to the --; | |
| " 3, | " 46 | There should be parentheses around "c"; | |
| " 3, | " 68 | "tranverses" should be -- traverses --. | |
| " 5, | " 41 | "conventiently" should be -- conveniently --. | |
| " 6, | " 3 | "steam" should be -- stream --. | |
| " 8, | " 5 | "fermento" should be -- fermentor --; | |
| " 8, | " 27 | "assists a" should be -- assists in --. | |
| " 12, | " 30 | "ten" should be -- then --; | |
| " 12, | " 58 | "membrane-tupe" should be -- membrane-type --. | |

Signed and Sealed this thirtieth Day of August 1977

[SEAL]

Attest:

RUTH C. MASON             C. MARSHALL DANN
Attesting Officer           Commissioner of Patents and Trademarks